United States Patent
Divi et al.

(10) Patent No.: US 7,968,732 B1
(45) Date of Patent: Jun. 28, 2011

(54) PROCESS FOR THE PREPARATION OF 5-BENZYLOXY-2-(4-BENZYLOXYPHENYL)-3-METHYL-1H-INDOLE

(75) Inventors: Murali Krishna Prasad Divi, Hyderabad (IN); Bolineni Nageswara Rao, Hyderabad (IN); Dandu Venkata Suresh, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 0 days.

(21) Appl. No.: 12/949,098

(22) Filed: Nov. 18, 2010

(51) Int. Cl.
*A61K 31/404* (2006.01)
*C07D 209/32* (2006.01)

(52) U.S. Cl. .......... 548/509; 548/469; 514/412
(58) Field of Classification Search .......... None
See application file for complete search history.

(56) References Cited

U.S. PATENT DOCUMENTS 5,998,402 A    12/1999    Miller

FOREIGN PATENT DOCUMENTS

| EP | 0082183 A1 | 10/1997 |
|---|---|---|
| WO | 2008098527 A1 | 8/2008 |

OTHER PUBLICATIONS

Chris P. Miller, et al. Design, Synthesis, and Preclinical Characterization of Novel, Highly Selective Indole Estrogens, Journal of Medicinal Chemistry, vol. 44, p. 1654-1657 Feb. 27, 2001.

*Primary Examiner* — Yong Chu
*Assistant Examiner* — Michael Barker
(74) *Attorney, Agent, or Firm* — Caesar, Rivise, Bernstein, Cohen & Pokotilow, Ltd.

(57) ABSTRACT

The present invention is related to a process for the preparation of 5-benzyloxy-2-(4-benzyloxyphenyl)-3-methyl-1H-Indole (formula-1, a useful intermediate for the synthesis of bazedoxifene) using 4-benzyloxy propiophenone and 4-benzyloxy phenyl hydrazine hydrochloride.

Formula-1

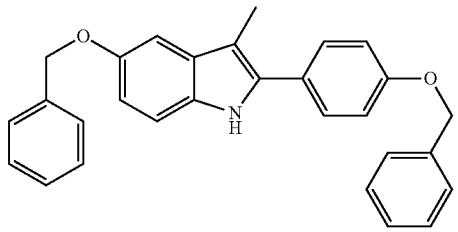

13 Claims, No Drawings

PROCESS FOR THE PREPARATION OF 5-BENZYLOXY-2-(4-BENZYLOXYPHENYL)-3-METHYL-1H-INDOLE

PRIORITY CLAIM

This application claims the benefit of the filing date of Indian priority application 2612/CHE/2010 filed on Sep. 9, 2010, the entire disclosure of which is incorporated by reference herein.

FIELD OF INVENTION

The present invention relates to a novel process for preparing 5-benzyloxy-2-(4-benzyloxyphenyl)-3-methyl-1H-Indole which is used for the production of bazedoxifene.

BACKGROUND OF THE INVENTION

Bazedoxifene is a third generation selective estrogen receptor modulator. It is used in the prevention and treatment of postmenopausal osteoporosis (Miller et al., EP0802183). Conventional processes for preparing 5-benzyloxy-2-(4-benzyloxyphenyl)-3-methyl-1H-indole are disclosed in U.S. Pat. No. 5,998,402, EP 0802183, World application WO-2008098527 and Journal of Medicinal Chemistry, 2001, volume 44, page no. 1654-1657.

The process disclosed in U.S. Pat. No. 5,998,402 may be summarized as following reaction Scheme-1.

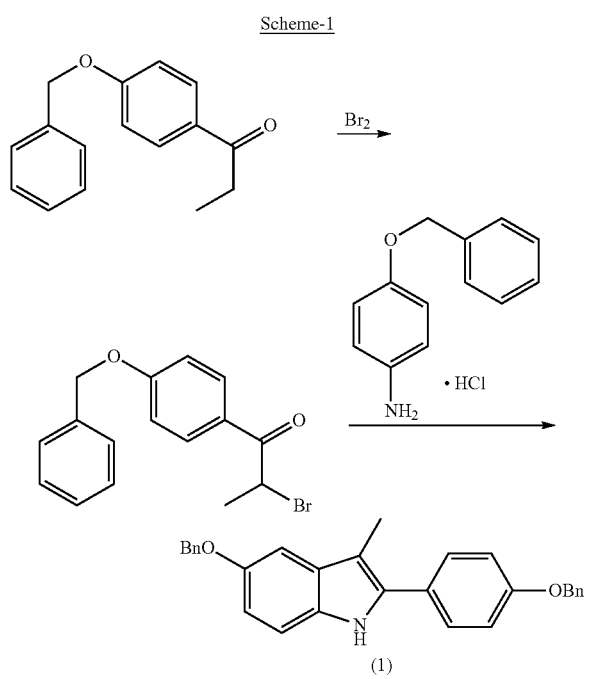

In the above process according to the reaction 2-bromo-4'-benzyloxy propiophenone is reacted with 4-benzyloxy aniline hydrochloride in dimethyl formamide. The process has the following disadvantages: The use of bromine calls for special safety measures and equipment to handle, the process involves isolation of bromo intermediate and results in only 33-54% overall yield. Hence the process is not economical.

The process disclosed in World application WO-2008098527 may be summarized in the following

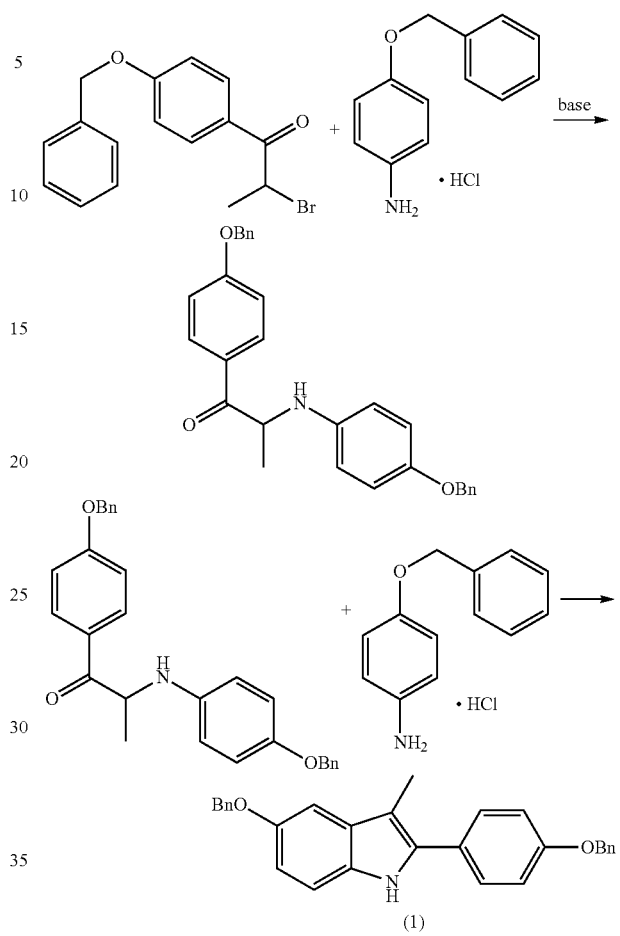

reaction Scheme-2.

The process is essentially similar to the scheme-1. In the above process, the intermediate N-(4-benzyloxyphenyl)-α-amino-4-benzyloxy propiophenone is isolated and treated with an excess of the aniline reagent to complete the cyclisation step. The reaction is carried out in an organic solvent and in the presence of an inorganic or an organic base from a group including sodium carbonate, potassium carbonate, triethylamine or diisopropylamine.

The process (Scheme-2) has the following disadvantages. A large excess of 4-benzyloxy aniline hydrochloride is required though later recovered through isolation from mother liquors. The overall yield is only 65-70%. The second step of the reaction is conducted in a pressure vessel at a temperature of 100-120° C. Hence the above process suffers from avoidable reaction conditions of reagent quantity, temperature and pressure.

Thus, there is a need for a simple, less cumbersome and better yielding process for the manufacture of 5-benzyloxy-2-(4-benzyloxyphenyl)-3-methyl-1H-indole of the formula-1, the key intermediate in the manufacture of bazedoxifene.

SUMMARY OF THE INVENTION

The present invention reveals a novel method for the preparation of 5-benzyloxy-2-(4-benzyloxyphenyl)-3-methyl-1H-indole, based on a Fischer indole synthesis.

DETAILED DESCRIPTION OF INVENTION

Surprisingly we found that the starting material 4-benzyloxy propiophenone (formula-2) reacts with 4-benzyloxy phenyl hydrazine hydrochloride (formula-3) in the presence of a Lewis or Bronsted acid in an organic solvent preferably a polar organic solvent as outlined in Scheme-3 below yielding the required indole compound in a single step.

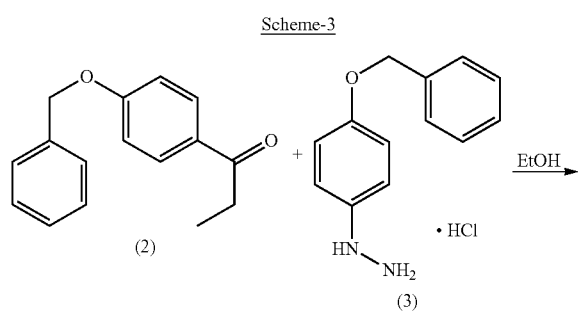

Scheme-3

Suitable acids for use in this reaction include Lewis acids such as $ZnCl_2$, $ZnBr_2$, $BF_3$, $FeCl_3$, $AlCl_3$, $SnCl_4$ and Bronsted acids such as acetic acid, hydrochloric acid, sulphuric acid, polyphosphoric acid, polyphosphate ester, p-toluene sulfonic acid, and methane sulfonic acid, but preferably acetic acid.

A suitable solvent used in the reaction includes a solvent or mixtures of solvents like $C_1$-$C_4$ alcohols or toluene, acetonitrile or mixtures thereof but preferably ethanol.

The temperature for conducting the reaction can range from about 0-140° C., preferably 75-80° C.

The product is isolated by filtration, the yield being 93-95% with high purity (>99%), which can be used without further purification in the next step.

The simple and new process of the present invention is industrially well suited, reproducible and commercially viable.

EXAMPLES

The invention is described in more detail in the following examples and do not limit the invention in any way. The reagents and solvents mentioned in examples are for illustration purpose only and may be replaced by other reagents and solvents known to those skilled in the art.

Preparation of 5-benzyloxy-2-(4-benzyloxyphenyl)-3-methyl-1H-indole (Formula-1)

Example-1

4-Benzyloxy phenyl hydrazine hydrochloride (1.0 g, 4 mmol), 4-benzyloxy propiophenone (0.96 g, 4 mmol) were suspended in 15 ml of ethanol and mixture was refluxed for 12 hrs at a temperature of 75-80° C. Then the mixture was cooled to 10-15° C. within 1 hr. The white product was filtered and washed with chilled ethanol (3 ml). The title compound 5-benzyloxy-2-(4-benzyloxy phenyl)-3-methyl-1H-indole (formula-1) melting at 152-153° C. and purity by HPLC 99.5% was obtained in a yield of 1.4 g (83.6%).

Example-2

4-Benzyloxy phenyl hydrazine hydrochloride (10 g, 40 mmol), 4-benzyloxy propiophenone (9.6 g, 40 mmol) and acetic acid (0.1 ml, 1.7 mmol) were suspended in 140 ml of ethanol and the mixture was refluxed for 12 hrs at a temperature of 75-80° C. During said period the product precipitates. After cooling the mixture at 10-15° C. the crystallized product was isolated by filtration and washed with chilled ethanol (30 ml) and water (50 ml). 5-Benzyloxy-2-(4-benzyloxy)-3-methyl-1H-indole melting at 152-153° C. was obtained in a yield of 15.7 g (94%).

$^1$H-NMR (DMSO) δ 10.65 (s, 1H); 7.55 (d, 2H); 7.50 (d, 4H); 7.30-7.45 (m, 6H); 7.21 (d, 1H); 7.10 (d, 1H); 7.10 (d, 1H); 6.91 (dd, 1H); 5.16 (s, 2H); 5.11 (s, 2H); 2.33 (s, 3H)

Example-3

4-Benzyloxy phenyl hydrazine hydrochloride (10 g, 40 mmol), 4-benzyloxy propiophenone (9.6 g, 40 mmol) and aluminium chloride (0.1 gm, 0.75 mmol) were suspended in 140 ml of ethanol and the mixture was refluxed for 12 hrs at a temperature of 75-80° C. During this period the product precipitates. After cooling the mixture to 10-15° C. the crystallized product was isolated by filtration and washed with chilled ethanol (30 ml) and water (50 ml). 5-Benzyloxy-2-(4-benzyloxy)-3-methyl-1H-indole melting at 152-153° C. was obtained in a yield of 15.0 g (90%).

Example-4

4-Benzyloxy phenyl hydrazine hydrochloride (10 g, 40 mmol), 4-benzyloxy propiophenone (9.6 g, 40 mmol) and acetic acid (0.1 ml, 1.7 mmol) were suspended in 140 ml of toluene and the mixture was refluxed for 12 hrs at the temperature of 105-110° C. During this period the product precipitates. After cooling the mixture to 10-15° C. the crystallized product was isolated by filtration and washed with toluene (30 ml) and water (50 ml). 5-Benzyloxy-2-(4-benzyloxy)-3-methyl-1H-indole melting at 149-150° C. was obtained in a yield of 10.0 g (60%).

Example-5

4-Benzyloxy phenyl hydrazine hydrochloride (1.0 g, 4 mmol), 4-benzyloxy propiophenone (0.96 g, 4 mmol) and acetic acid (10 μl, 0.17 mmol) were suspended in 15 ml of acetonitrile and the mixture was refluxed for 12 hrs at a temperature of 81-82° C. Then mixture was cooled to 10-15° C. within 1 hr. The white product was filtered and washed with chilled acetonitrile (3 ml). 5-Benzyloxy-2-(4-benzyloxy phenyl)-3-methyl-1H-indole (1) melting at 149-150° C. was obtained in a yield of 1.0 g (60%).

We claim:

1. A process for the preparation of 5-benzyloxy-2-(4-benzyloxy phenyl)-3-methyl-1H-indole (formula-1);

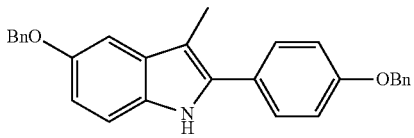
(1)

which comprises reacting 4-benzyloxy propiophenone of formula-2 with 4-benzyloxy phenyl

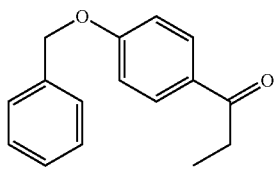
(2)

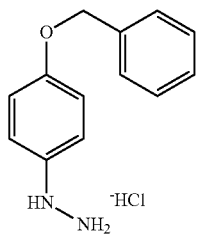
(3)

hydrazine or its hydrochloride of formula-3 in an organic solvent and at a temperature from 0° C.-140° C. in the presence an acid catalyst.

2. The process according to claim 1, wherein the reaction is carried out in an organic solvent selected from the group of $C_1$-$C_4$ alcohols, toluene and acetonitrile or mixtures thereof.

3. The process according to claim 1, wherein the acid catalyst used is a Bronsted acid or a Lewis acid.

4. The process according to claim 3, wherein the Bronsted acid is selected from the group consisting of acetic acid, hydrochloric acid, sulphuric acid, polyphosphoric acid, polyphosphate ester, p-toluene sulfonic acid, and methane sulfonic acid.

5. The process according to claim 3, wherein the Lewis acid is selected from the group consisting of $ZnCl_2$, $ZnBr_2$, $BF_3$, $FeCl_3$, $AlCl_3$, and $SnCl_4$.

6. The process according to claim 1, wherein the reaction is carried out at 0° C.-140° C., preferably at 75° C.-80° C.

7. The process according to claim 2, wherein the reaction is carried out at 0° C.-140° C., preferably at 75° C.-80° C.

8. The process according to claim 3, wherein the reaction is carried out at 0° C.-140° C., preferably at 75° C.-80° C.

9. The process according to claim 4, wherein the reaction is carried out at 0° C.-140° C., preferably at 75° C.-80° C.

10. The process according to claim 5, wherein the reaction is carried out at 0° C.-140° C., preferably at 75° C.-80° C.

11. The process according to claim 2, wherein the preferred solvent is ethanol.

12. The process according to claim 3, wherein the preferred acid catalyst is acetic acid.

13. The process according to claim 4, wherein the reaction is carried out at reflux temperature of the solvent used.

* * * * *

UNITED STATES PATENT AND TRADEMARK OFFICE
CERTIFICATE OF CORRECTION

| | | |
|---|---|---|
| PATENT NO. | : 7,968,732 B1 | Page 1 of 1 |
| APPLICATION NO. | : 12/949098 | |
| DATED | : June 28, 2011 | |
| INVENTOR(S) | : Murali Krishna Prasad Divi et al. | |

It is certified that error appears in the above-identified patent and that said Letters Patent is hereby corrected as shown below:

On the Title Page Item (30) should read:

Item --(30)     Foreign Application Priority Data

September 7, 2010     (IN).................2612/CHE/2010--

In the Specifications:

In Column 1, Line 8, replace with:
--Indian priority application 2612/CHE/2010 filed on Sep. 7,--

Signed and Sealed this
Thirteenth Day of November, 2012

David J. Kappos
*Director of the United States Patent and Trademark Office*